US008403224B2

(12) United States Patent
Fedorko et al.

(10) Patent No.: US 8,403,224 B2
(45) Date of Patent: Mar. 26, 2013

(54) APPARATUS, SYSTEM AND METHOD FOR TRACKING DRUGS DURING A REPACKAGING AND ADMINISTERING PROCESS

(75) Inventors: Ludwik Fedorko, Mississauga (CA); Joseph Fisher, Thornhill (CA); Bryan Drew Miller, Richmond Hill (CA); Bryan Kowalchuk, Oakville (CA)

(73) Assignee: University Health Network, Toronto (CA)

( * ) Notice: Subject to any disclaimer, the term of this patent is extended or adjusted under 35 U.S.C. 154(b) by 628 days.

(21) Appl. No.: 12/015,809

(22) Filed: Jan. 17, 2008

(65) Prior Publication Data
US 2008/0314978 A1    Dec. 25, 2008

Related U.S. Application Data

(63) Continuation-in-part of application No. PCT/CA2007/001421, filed on Mar. 17, 2007.

(60) Provisional application No. 60/910,451, filed on Apr. 5, 2007, provisional application No. 60/822,509, filed on Aug. 15, 2006.

(51) Int. Cl.
*G06K 7/10*    (2006.01)

(52) U.S. Cl. .................. 235/470; 235/454; 235/462.01; 235/487

(58) Field of Classification Search .................. 235/385, 235/454, 462.01, 470, 487
See application file for complete search history.

(56) References Cited

U.S. PATENT DOCUMENTS 4,476,381 A * 10/1984 Rubin ........................... 235/375
(Continued)

FOREIGN PATENT DOCUMENTS

CA    2534596    7/1997

OTHER PUBLICATIONS

"Comment regarding requirement for drug barcode labelling" (online) <URL:http://www.fda.gov/ohrms/dockets/dailys/03/Jun03/061203/02n-0204-c000067-01-vol14.pdf>, Jun. 2, 2003.

*Primary Examiner* — Daniel Hess
*Assistant Examiner* — Paultep Savusdiphol
(74) *Attorney, Agent, or Firm* — Klein, O'Neill & Singh, LLP

(57) ABSTRACT

The invention relates to a system and method for tracking drugs during a transfer and administering process to reduce labeling errors that can occur during that process. The system includes a storage container reader that is configured to read a set of one or more storage-container-associated machine-readable indicia positioned on a container containing a drug. The set of one or more storage-container-associated machine-readable indicia identifies the drug. The system further includes an indicia-generating device that is configured to generate a drug-delivery-container-associated indicia identifying the drug based on the storage-container-associated machine-readable indicia. The set of one or more drug-delivery-container-associated indicia includes a set of one or more drug-delivery-container-associated machine-readable indicia. Optionally the system further includes a drug delivery container reader, wherein the drug delivery container reader is configured to read the set of one or more drug-delivery-container-associated machine-readable indicia. Optionally the system further includes a processing unit that generates an output signal corresponding to the drug based on the set of one or more drug-delivery-container-associated machine-readable indicia. Optionally the system further includes an output device that outputs a user-comprehensible output identifying the drug based on the output signal from the processing unit.

26 Claims, 5 Drawing Sheets

U.S. PATENT DOCUMENTS

| | | | |
|---|---|---|---|
| 4,652,317 A | 3/1987 | Seestrom | |
| 5,621,864 A * | 4/1997 | Benade et al. | 358/1.18 |
| 5,651,775 A * | 7/1997 | Walker et al. | 604/207 |
| 5,781,442 A * | 7/1998 | Engleson et al. | 700/214 |
| 5,974,230 A * | 10/1999 | Jenkins | 358/1.9 |
| 6,519,569 B1 * | 2/2003 | White et al. | 705/3 |
| 6,671,563 B1 * | 12/2003 | Engelson et al. | 700/2 |
| 6,685,678 B2 * | 2/2004 | Evans et al. | 604/207 |
| 6,985,870 B2 * | 1/2006 | Martucci et al. | 705/3 |
| 6,994,249 B2 * | 2/2006 | Peterka et al. | 235/375 |
| 7,154,397 B2 * | 12/2006 | Zerhusen et al. | 340/573.1 |
| 7,236,936 B2 * | 6/2007 | White et al. | 705/3 |
| 7,240,841 B2 * | 7/2007 | Kelley et al. | 235/462.01 |
| 7,668,731 B2 * | 2/2010 | Martucci et al. | 705/2 |
| 8,140,349 B2 * | 3/2012 | Hanson et al. | 705/2 |
| 2003/0009244 A1 * | 1/2003 | Engleson et al. | 700/86 |
| 2003/0052787 A1 * | 3/2003 | Zerhusen et al. | 340/573.1 |
| 2003/0120384 A1 * | 6/2003 | Haitin et al. | 700/242 |
| 2003/0135388 A1 * | 7/2003 | Martucci et al. | 705/2 |
| 2004/0054436 A1 * | 3/2004 | Haitin et al. | 700/236 |
| 2004/0104271 A1 * | 6/2004 | Martucci et al. | 235/472.01 |
| 2004/0243434 A1 * | 12/2004 | Peterka et al. | 705/2 |
| 2006/0177637 A1 * | 8/2006 | Kimura | 428/195.1 |

* cited by examiner

APPARATUS, SYSTEM AND METHOD FOR TRACKING DRUGS DURING A REPACKAGING AND ADMINISTERING PROCESS

This application is a continuation-in-part of PCT Application No. PCT/CA2007/001421 filed Aug. 15, 2007, the disclosure of which is hereby incorporated by reference.

FIELD OF THE INVENTION

The invention relates to reducing errors in, the identification of drugs in a repackaging and administering process, in particular where the repackaging takes place at the point-of-care.

BACKGROUND OF THE INVENTION

Prior to administering a drug to a patient, the drug may require transfer from a storage container to a drug delivery container. The storage container may be, for example, a single-dose drug container. The drug delivery container may be, for example, a syringe. Typically, after the drug is transferred to the syringe, the person carrying out the transfer sometimes prepares a label by hand and applies it to the syringe to indicate the drug now contained in the syringe. In some situations, pre-prepared labels are provided to eliminate the need for the person to manually prepare the label. Some systems have been provided whereby the person can type in the name of the drug into a computer to print a label instead of having to prepare the label manually.

Several different types of error can occur during this process all of which can lead to the syringe bearing a label indicating a different drug than is actually contained in the syringe. For example, the user can pull the wrong drug from a drug cabinet and prepare a label with the name of the drug they thought they pulled. This can occur particularly easily with certain drugs, because their colour and packaging may be quite similar.

Alternatively, the user may pull the correct drug from the drug cabinet, but may inadvertently prepare a label indicating the next drug that has to be prepared because that next drug is on the user's mind at the time. Another problem is that some drugs have very similar names to other drugs, which increases the risk that a user will mistake one drug for another.

Once a syringe is mis-labeled many problems can occur. If a patient receives the wrong drug, this can lead to catastrophic consequences. Unfortunately, doctors treating the patent might not find out the true cause of the patient's reaction and therefore would not be easily able to properly treat it.

A proposed solution to this problem has been to prepare and label syringes at the pharmacy and to send the drugs to the point of care in the syringes to eliminate the need for a repackaging step. A problem with this approach is that the drugs expire relatively quickly once they are in the syringe, and often the drug manufacturer is not certain how quickly. In many cases, the drug expires in a matter of hours.

Additionally, storage of the drug in a syringe over several hours can in some situations lead to chemicals contained in the syringe components (eg. housing, plunger and seal) leaching into the drug. If the patient reacts to these chemicals this can cause harm to the patient.

Additionally, in some environments, such as an operating room environment, it sometimes occurs that an unexpected drug is required to be administered to the patient. Either the drug has to be repackaged in the operating room with all of its inherent problems as described above, or the pharmacy has to prepare many extra syringes containing drugs to cover off unexpected situations. Whichever of these extra syringes is not used during the operation is discarded, since they cannot be repackaged with confidence in their expiry date or their safety. This practice is, of course, wasteful of the discarded drugs and may also be costly.

SUMMARY OF THE INVENTION

In a first aspect, the invention relates a method for tracking drugs during a transfer and administering process, wherein a drug is transferred from a storage container to a drug delivery container, and wherein a container containing a drug is withdrawn from a source of drugs, wherein the container has thereon a set of one or more storage-container-associated machine-readable indicia identifying the drug, the method comprising:

a) providing a reader/indicia-generating device including a storage container reader and an indicia/generating device at the point of care of a patient, wherein the storage container reader is configured to read the set of one or more storage-container-associated machine-readable indicia and wherein the indicia-generating device is configured to generate a set of one or more drug-delivery-container-associated indicia identifying the drug, based on the set of one or more storage-container-associated machine-readable indicia;

b) causing the storage-container-associated machine-readable indicia to be read by the storage container reader so that the storage container reader/indicia-generating device prepares the set of one or more drug-delivery-container-associated indicia;

c) transferring the drug into the drug delivery container from the container; and d) applying the set of one or more drug-delivery-container-associated indicia to the drug delivery container.

In a second aspect, the invention relates to a system for tracking drugs during a transfer and administering process. The system includes a storage container reader that is configured to read a set of one or more storage-container-associated machine-readable indicia positioned on a container containing a drug. The set of one or more storage-container-associated machine-readable indicia identifies the drug. The system further includes an indicia-generating device that is configured to generate a drug-delivery-container-associated indicia identifying the drug based on the storage-container-associated machine-readable indicia. The set of one or more drug-delivery-container-associated indicia includes a set of one or more drug-delivery-container-associated machine-readable indicia.

In a third aspect, the invention relates to a system for tracking drugs during a transfer and administering process to reduce labeling errors that can occur during that process. The system includes a storage container reader that is configured to read a set of one or more storage-container-associated machine-readable indicia positioned on a container containing a drug. The set of one or more storage-container-associated machine-readable indicia identifies the drug. The system further includes an indicia-generating device that is configured to generate a drug-delivery-container-associated indicia identifying the drug based on the storage-container-associated machine-readable indicia. The set of one or more drug-delivery-container-associated indicia includes a set of one or more drug-delivery-container-associated machine-readable indicia. The system further includes a drug delivery container reader, wherein the drug delivery container reader is configured to read the set of one or more drug-delivery-container-associated machine-readable indicia. The system further includes a processing unit that generates an output signal corresponding to the drug based on the set of one or more drug-delivery-container-associated machine-readable indicia. The system further includes an output device that outputs a user-comprehensible output identifying the drug based on the output signal from the processing unit.

In a fourth aspect, the invention relates a method for tracking drugs during a transfer and administering process, wherein a drug is transferred from a storage container to a drug delivery container, and wherein a container containing a drug is withdrawn from a source of drugs, wherein the container has thereon a set of one or more storage-container-associated machine-readable indicia identifying the drug, the method comprising:

a) providing a storage container reader and a controller at the point of care of a patient, wherein the storage container reader is configured to read the set of one or more storage-container-associated machine-readable indicia and wherein the controller is configured to generate an output signal to control the output of a set of one or more drug-delivery-container-associated indicia identifying the drug, based on the set of one or more storage-container-associated machine-readable indicia; and b) causing the storage-container-associated machine-readable indicia to be read by the storage container reader to cause an output signal to be generated to control the output of the set of one or more drug-delivery-container-associated indicia.

In another aspect, the invention relates to a system for reducing certain kinds of errors during a drug transfer process from a drug container to a drug delivery container, such as a syringe.

In another aspect, the invention relates to a method for reducing certain kinds of errors during a drug transfer process from a drug container to a drug delivery container, such as a syringe.

Other aspects and features of the present invention will become apparent, to those ordinarily skilled in the art, upon review of the following description of the specific embodiments of the invention.

In another aspect, the invention is directed to a label adapted for color coding the drug content of drug delivery container, for example a syringe, the label comprising a plurality of different colored regions, corresponding in a full set or subset of different colors belonging to a color-based drug identification or coding standard, for example a color coding standard for classes of drugs. The label may be constituted to be best used with a particular printing technology for example thermal or laser printers. Such a label may be provided on sheets or rolls that are adapted to be advanced area by area e.g. row by row, or sheet by sheet by the printer for which they are designed so that the labels can be printed singly or in groups, optionally using technology that prevent smudging, for example using laser or thermal printers. Such colored regions are sized and positioned to be over-printed, for example with a printer, optionally a one or two color capable printer, optionally a printer that prints only in dark color e.g. black, to neutralize or make uniform (e.g. by masking, partially or completely), all colors but the one particular color that corresponds to the drug or class of drug that identifies the drug content of the drug delivery container. In this way this particular color stands out and suitably represents the correct color coding of the label in accordance with the standard. The color region that stands out may have a particular hatching additionally printed thereon to more particularly identify the drug. In another related aspect the invention is directed to label so masked with at least one unmasked original color region corresponding per the standard to the drug content (e.g. class) remaining unmasked, this latter region optionally hatched. In another related aspect the invention is directed to a method of color coding a drug delivery container comprising the steps of providing a label that is pre-printed with colored regions as aforesaid and printing thereon a color that masks all the regions except for the at least one region bearing the color that identifies the drug or class of drug as per the standard. The aforesaid method may include the further step of applying the printed label to the drug delivery container. When used with a set of labels adhered to a backing (rolled or in a sheet), this method enables drug delivery containers to be color-coded, label by label, using an indicia generating device at the point of care. Alternatively, the label may be provided, pre-affixed (to the drug delivery container) and the printing (color-masking and optionally hatch-marking) step may be carried out directly on the container label. The term "pre-affixed", as used herein broadly contemplates methods of applying these regions of color onto the material of the drug-delivery container (other than by applying a separate label) by "printing" these regions directly onto this material and the invention is directed to a drug delivery container with such applied color regions as well as containers further printed with color-masking printed matter which isolates the drug identification color as per the standard as described above and optionally hatch marks. Color-coded labels or drug-delivery containers as aforesaid may further comprise other machine and/or human readable indicia of content and other useful information as described herein. In one embodiment of the invention, the additional indicia are a machine readable code, for example, a bar code that operates with a method or system for tracking drugs during an administering process or during a transfer and administering process (as defined above) the system including a drug delivery container reader that is configured to read the machine-readable indicia and a speaker to announce indicia borne information pertaining to the identity of the drug comprising the name of the drug In a more general aspect, the invention is directed to method or system for tracking drugs during an administering process or during a combined transfer and administering process in which labeled drug delivery containers, whether color coded or not, bearing machine readable indicia (and optionally other indicia, for example, meaningful human-readable letters, symbols or words in a language of choice) pertaining to the drug content are audibly sounded. Using the system or carrying out the method comprises the step of passing the drug delivery container in proximity to a reader and listening to a speaker used to announce indicia borne information pertaining to the identity of the drug comprising the name of the drug. By audibly sounding the information borne by the machine readable indicia comprising at least the name of drug the drug's identity may be confirmed immediately prior to administration.

The color coding aspect of the invention may be integrated as part of any method or system of tracking drugs identified herein and reader/indicia generating device contemplated herein.

Accordingly, for example, in one embodiment, the invention is directed to a method for tracking drugs during an administering process, the method comprising:

a) providing an indicia-generating device at the point of care of a patient, wherein the indicia-generating device is configured to generate a set of one or more drug-delivery-container-associated indicia identifying the drug including a color code;

b) causing the indicia-generating device: to prepare a set of one or more drug-delivery-container-associated indicia including a color code;

and wherein the indicia generating device generates a color code by over-printing regions of different color pre-printed on a label to mask those regions except for the region of color corresponding to identity of the drug.

Accordingly, for example, in one embodiment, the invention is directed to a method for tracking drugs during a transfer and administering process, wherein a drug is transferred from a storage container to a drug delivery container, and wherein a container containing a drug is withdrawn from a source of drugs, wherein the container has thereon a set of one or more storage-container-associated machine-readable indicia identifying the drug, the method comprising:

a) providing a storage container reader and an indicia-generating device at the point of care of a patent, wherein the storage container reader is configured to read the set of one or more storage-container-associated machine-readable indicia and wherein the indicia-generating device is configured to generate a set of one or more drug-delivery-container-associated indicia identifying the drug including a color code, based on the set of one or more storage-container-associated machine-readable indicia;

b) causing the storage-container-associated machine-readable indicia to be read by the storage container reader so that the indicia-generating device prepares the set of one or more drug-delivery-container-associated indicia including a color code;

and wherein the indicia generating device generates a color code by over-printing regions of different color pre-printed on a label to mask those regions except for the region of color corresponding to identity of the drug.

Optionally, the colored regions correspond to a standard for identifying classes of drugs. Optionally, the standard includes indicia comprising hatch marks. Optionally, the indicia generating device applies hatch marks to the unmasked colored region corresponding to the identity of the drug or class of drug. Optionally the indicia generating device prepares a separate label for application to the drug delivery container. Optionally the label is directly printed onto the drug delivery container. Alternatively the label is a separate label pre-affixed to the container. In either and the indicia generating device may prints the drug-delivery-container-associated indicia directly on the drug delivery container.

Optionally, for example, the method or system may comprise one or more the following additional steps:

c) transferring the drug into the drug delivery container from the container; and d) providing a drug delivery container reader at the point of care of a patient, wherein the reader is configured to read the set of one or more delivery-container-associated machine-readable indicia;

f) causing the delivery-container-associated machine-readable indicia to be read by the reader; and g) providing an output device that outputs a user-comprehensible output, for example, a speaker for generating audibly sounded drug identity information corresponding to the drug-delivery-container-associated indicia.

The storage container reader and the drug delivery container reader may be one in the same component so that step e) is superfluous, having been accomplished in step a).

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which.

DETAILED DESCRIPTION OF THE INVENTION

Figure 1:
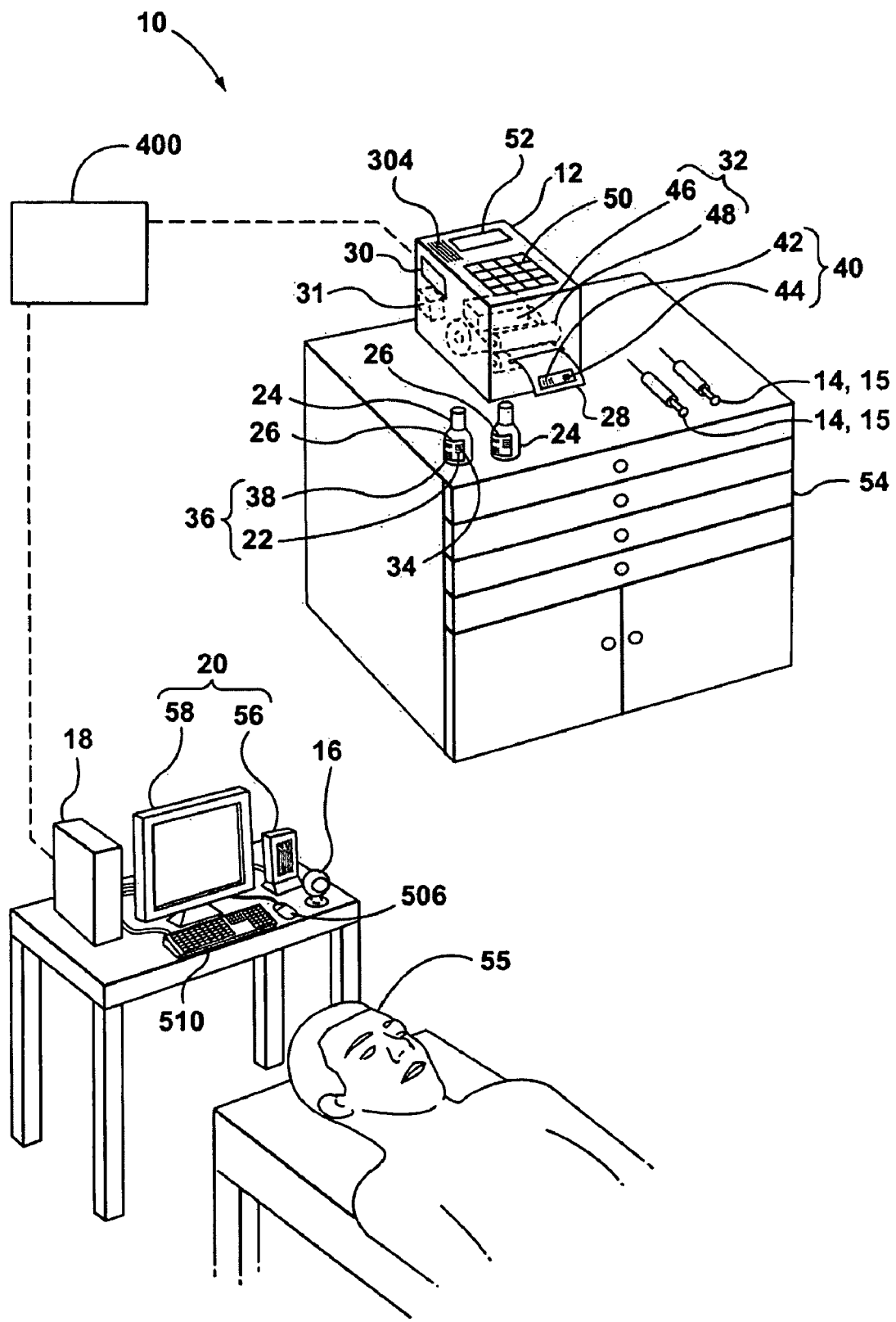
FIG. 1 is a perspective view of a system for tracking drugs during a transfer and administering process in accordance with an embodiment of the invention.

Reference is made to FIG. 1, which shows a system 10 for tracking drugs during a drug transfer and administering process in accordance with an embodiment of the present invention. Drug transfer may also be referred to as drug repackaging.

In many environments, such as an operating room, a recovery room and a critical care room, a drug 26 is transferred from a storage container 24 to a drug delivery container 14, such as a syringe 15. The system 10 permits the applying of a set of one or more drug identification indicia 40 on the drug delivery container 14 with a reduced degree of error over some prior art systems and methods.

The system 10 includes a reader/indicia-generating device 12 and optionally further includes a drug delivery container reader 16, a processing unit 18, and an output device 20. The reader/indicia-generating device 12 is used to read a set of one or more storage-container-associated machine-readable indicia 22 that are present on the drug storage container 24. The reader/indicia-generating device 12 outputs a set of one or more drug-delivery-container-associated drug identification indicia 40 that is applied to the drug delivery container 14, wherein the set of one or more drug-delivery-container-associated indicia 40 is based on the storage-container-associated machine-readable drug identification indicia 22.

The reader/indicia-generating device 12 includes a storage container reader 30, a controller 31 and an indicia-generating device 32. The storage container reader 30 is configured to read a set of one or more storage-container-associated machine-readable indicia 22 positioned on the drug storage container 24. The storage-container-associated machine-readable drug identification indicia 22 identify the drug 26 contained in the container 24. The set of one or more storage-container-associated machine-readable drug identification indicia 22 may be any suitable type of indicia, such as, for example, a, bar-code, a numeric code or text. It is possible that the set may include as few as a single indicium 22.

The storage-container-associated machine-readable drug identification indicia 22 may be provided on the storage container 24 in any suitable way. For example, the storage-container-associated machine-readable drug identification indicia 22 may be present as indicia directly on the storage container 24 itself, or may be provided on a label 34 that is associated with the storage container 24 (ie. connected to the container 24 in any suitable way). Alternatively, the storage-container-associated machine-readable drug identification indicia 22 may be provided on an electronic ID device that is associated with the storage container 24 (ie. connected to the container 24 in any suitable way). For example, the identification indicia 22 could be provided on an RF-ID tag, or could be provided oh an ID chip that stores the indicia 22 and transmits them in the form of signals that are received by the storage container reader 30.

The storage-container-associated machine-readable drug identification indicia 22 may be part of a set of one or more storage-container-associated indicia 36 on the storage container 24 that may also include a set of one or more storage-container-associated user-readable indicia 38, which identifies the drug 26 in a way that is readable by a person. For example, the storage-container-associated user-readable indicia 38 may simply be text. It is possible that the set may include as few as a single indicium 38.

It will be appreciated that in some instances, the same indicia may be readable by both a user and by a machine. For example, if the set of one or more storage-container-associated user-readable indicia 38 is made up of text, the text may also be readable by an appropriate type of container reader 30. Accordingly, the text may also serve as the storage-container-associated machine-readable drug identification indicia 22.

The storage container reader 30 may be any suitable reading device that is capable of reading the storage-container-associated machine-readable drug identification indicia 22. For example, the storage container reader 30 may be a bar-code reader in an embodiment wherein the set of one or more storage-container-associated machine-readable drug identification indicia 22 is a bar code. Preferably, in embodiments wherein the set of one or more storage-container-associated machine-readable drug identification indicia 22 is a bar code, the storage container reader 30 is a linear laser scanner type of bar code reader. This type of bar code reader is capable of reading bar codes which are high-density and/or small, which may, for example, be present on smaller drug ampules.

Alternatively, in embodiments wherein the identification indicia 22 are provided electronically by means of an RF-ID tag or in some other electronic form on a chip, the storage container reader 30 may be a suitable receiver for receiving signals from the RF-ID tag or ID chip or other electronic ID device.

More specifically, in embodiments wherein the storage container reader 30 is a bar-code reader, it may be a linear imager scanner type of bar-code reader.

The controller 31 receives from the reader 30 a signal relating to the storage-container-associated machine-readable indicia 22. The controller 31 generates and transmits an output signal by any suitable means to the indicia-generating device 32 to control the output of the set of one or more drug-delivery-container-associated indicia 40. The output signal may be sent via a suitable conduit 41, such as an electrical wire. Alternatively, the output signal may be sent wirelessly by any suitable wireless means.

The indicia-generating device 32 is configured to generate the set of one or more drug-delivery-container-associated indicia 40 which identify the drug 26, based on the storage-container-associated machine-readable indicia 22. The set of one or more drug-delivery-container-associated indicia 40 may include a set of one or more drug-delivery-container-associated machine-readable drug identification indicia 42, such as, for example, a bar code. It is possible that the set may include as few as a single indicium 42. Additionally or alternatively the drug-delivery-container-associated indicia 40 may include a set of one or more drug-delivery-container-associated user-readable drug identification indicia 44, such as text. It is possible that the set may include as few as a single indicium 44.

It will be appreciated that in some instances, the same indicia may be readable by both a user and by a machine. For example, if the set of one or more drug-delivery-container-associated user-readable indicia 44 is made up of text, the text may be text may be readable by an appropriate type of drug delivery container reader 16. Accordingly, the text may also serve as the drug-delivery-container-associated machine-readable drug identification indicia 42.

The indicia-generating device 32 may provide the drug identification indicia 40 on a drug delivery, container label 28, which is applied to the drug delivery container 14. The indicia-generating device 32 may be, for example, a printer 46 with a feed mechanism 48 for printing and advancing a drug delivery container label 28. The printer 46 could be, for example, an inkjet printer or some other suitable type of printer. The drug delivery container label 28 may be a self-adhesive label that can be removed from a backing paper and applied to the drug delivery container 14.

The printer 46 could also print the label 28 in such a way as to colour code the label 28 to indicate the class of drug 26 contained in the drug delivery container 14. Some hospitals require such colour coding to provide a general indication to the user that the drug contained in the delivery container 14 is a stimulant, or a depressant, or some other class of drug 26. Such color coding may be mandated or recommended by certain professional regulatory bodies, for example the American Society of Anesthesiologists. Color coding can serve to quickly flag the user that the drug is of a certain class even if the user does not take the time to read any text that might be present on the label 28.

The printer 46 may be any suitable type of printer. For example, the printer 46 may advantageously be a thermal printer or a laser printer, as these technologies are less likely to result in smudging of the printed indicia 40 during handling of the drug delivery container 14 in embodiments wherein the indicia 40 are printed on labels 28. To maintain a compact size, the printer 46 prints in only a single colour, such as black, or white.

Figure 4A:
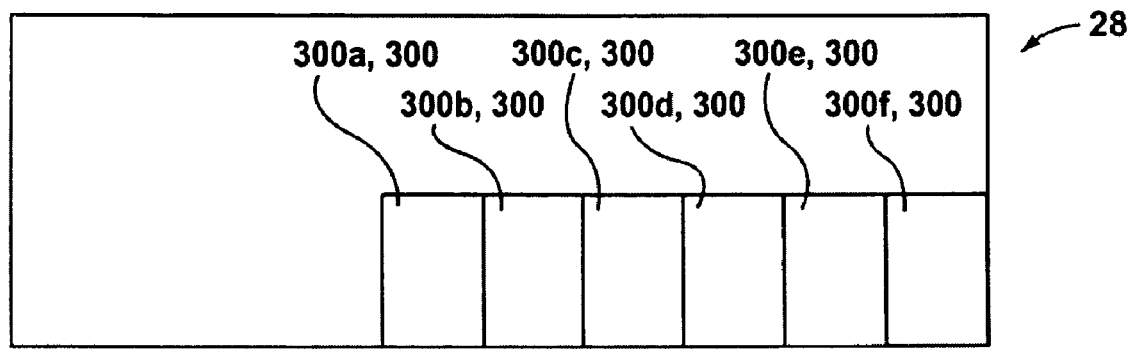
FIG. 4a is a representation of a drug delivery container label provided by the system of the present disclosure after a first stage of printing.
Figure 4B:
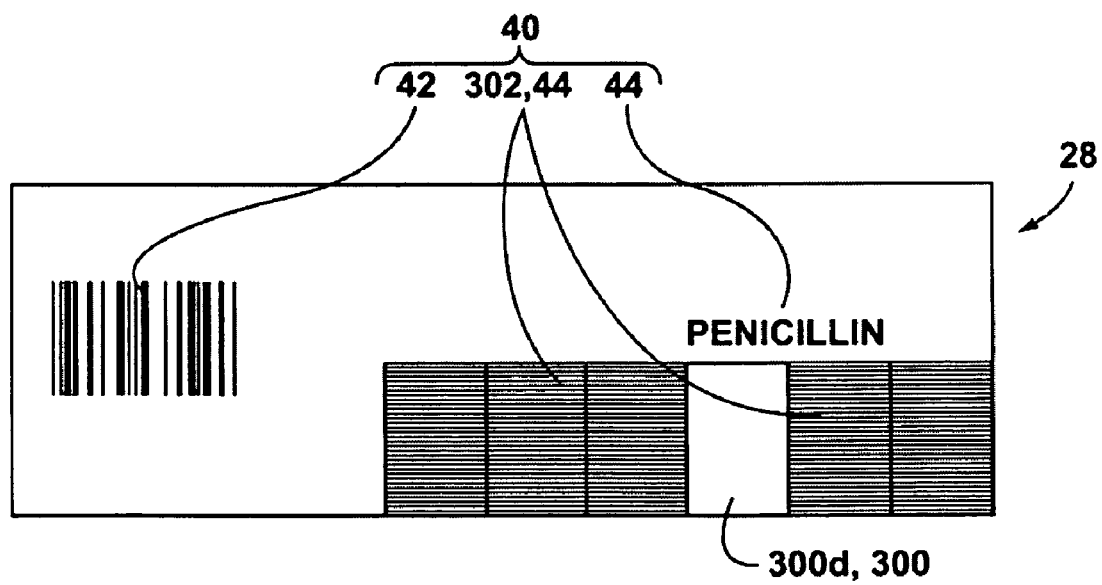
FIG. 4B is a representation of the drug delivery container label of FIG. 4a after a second stage of printing.

In order to provide the aforementioned colour coding on the label 28 when the printer 46 is capable of printing only a single colour, such as black, the printer 46 may use labels 28 such as that shown in FIG. 4a. The label 28 shown in FIG. 4a has pre-printed thereon a plurality of coloured regions 300, with each coloured region 300 being a unique colour. Thus, by way of example only, the region shown at 300a may be yellow, the region 300b may be blue, the region 300c may be pink, the region 300d may be green, the region 300e may be red and the region 300f may be brown, whereby each colour indicates a particular class of drug. Referring to FIG. 4b, when printing the label 28 with the indicia 40, the printer 46 could print over all of the regions 300 that do not represent the class of the drug identified on the label 28, thereby leaving exposed only the coloured region (which is 300d in the example shown in FIG. 4b) that does represent the class of the drug. In this way the printer 46 provides colour coding representation for the class of the drug 26 without having to be capable of colour printing. The one or more printed-over regions are shown at 302, and may be considered to be a type of user-readable indicia 44 which identify the drug 26 at least somewhat (ie. the drug's class).

It is preferable, though not necessary for the colour in which the printer 46 prints to be different than the colours that are present in the colour-coding regions 300. This may be less-confusing to the person who reviews the label afterwards to see what class of drug 26 is contained in the drug delivery container 14.

In an alternative embodiment, the indicia-generating device 32 may be a printing device that prints directly on the drug delivery container 14. In such an embodiment, the drug delivery container 14 may be held in a suitable cradle (not shown) adjacent the indicia-generating device 32. Printing directly on the drug delivery container 14 would save a step in the procedure, thereby saving time. This can be particularly useful in some environments, such as in an operating room environment in order to save time.

The reader/indicia-generating device 12 may include several other optional items, such as a keypad 50, a display 52 and a speaker 304. The keypad 50 permits the user to input information relating to the anesthesiologist and/or the doctor and/or the patient, shown at 55 in FIG. 1. The display 52 permits the user to see what has been inputted via the keypad 50 and/or other information.

The speaker 304 may provide audio output identifying the drug 26. Thus, when the storage container 24 is scanned, the name of the drug 26 may be said through the speaker 304. A user who may have inadvertently brought the wrong storage container 24 to be scanned would therefore receive a verbal indication of what the drug 26 container therein is. The display 52 may also serve the purpose of indicating to the user the drug 26 that has been scanned, however, it is possible for the user to proceed to print the label 28 without paying attention to the display 52, whereas verbal indication of the drug 26 using the speaker 304 is heard by the user regardless of where the user's attention is.

In embodiments wherein the patient 55 is identified to the reader/indicia-generating device 12 (eg. by entering the patient's MRN (medical record number) into the device 12), the reader/indicia-generating device 12 may be provided with patient-specific warning capability. For example, the device 12 may verbally indicate the name of the patient 55 and request that the user confirm that that is the correct patient. This is useful in embodiments when the user enters only an MRN for the patient, instead of the patient's name. As another example, the reader/indicia-generating device 12 may connect with the patient management system 400 of the patient care facility. Each storage container 24 that is scanned by the device 12 may be checked by the device 12, or by the patient management system 400, to verify one or more of the following conditions: whether there are any potentially harmful interactions with any of the other drugs that the patient 55 may currently be taking; whether there are any potentially harmful interactions with any of the other drugs that have been scanned into the device 12 for the patient 55, that the patient 55 is expected to receive shortly and whether the patient 55 is allergic to the drug 26. If the device 12 or patient management system 400 detects a problem (eg. the patient's record indicates that he/she is allergic to the scanned drug 26), then the device 12 may issue an audible and/or visual warning.

Another condition that the device 12, or the patient management system 400, may check is whether the scanned drug 26 is unexpected for the patient 55, given the patient care facility's schedule for the patient. For example, if the patient is not expected in surgery, the device 12 may issue a warning in the event that the user scans a container 24 that contains an anaesthetic drug or some other drug generally associated with surgery.

In general, if the device 12 issues a warning regarding a particular drug 26, the device 12 may be provided with the capability to receive information identifying the user to authenticate the user and permit the user to override the warning and permit the use of the drug. For example, the user may present the device's reader 30 with a bar-code that identifies him/her. The bar-code may be provided on an identification tag that is carried by the user.

Under selected conditions, the device 12 could be made not to print a label 28. For example, the device 12 may be programmed to not print a label 28 under any of the aforementioned conditions, if a user fails to authenticate themselves and override the warning.

In embodiments wherein patient information (eg. patient name) is inputted to the reader/indicia-generating device 12, eg. by means of the keypad 50, some or all of this information may be outputted from the indicia-generating device 32 as indicia for appearing on the drug delivery container 14. Using a human interface input device such as touch screen, keyboard, mouse, microphone etc. the health care provider may input additional information such as the volume of diluents added to the drug, if any, type of diluents (e.g. water, saline, dextrose 5% solution, alcohol, etc.) and an exact volume drawn into the syringe (when different from the total volume of the drug in the original container). For example, the health care provider may take 3 ml of drug from a 10 ml container and dilute it into a final volume of 10 mls to make a water solution so that the final volume of the liquid contained in the syringe is 10 ml but only at 30% of the initial concentration of the drug in the ampoule. All this information may output by the indicia generating device onto a label to be applied to the drug delivery container. In addition because the drug is dispensed at the time of printing of the drug delivery container label, or immediately prior, automated calculation of a specific time of drug expiry may be counted from the moment of the storage container is scanned.

Additionally or alternatively, other information may also be outputted from the indicia-generating device 32 for appearance on the drug delivery container 14. For example, the date and time of transfer of the drug 26 from the storage container 24 to the drug delivery container 14 may be outputted as indicia on the drug delivery container 14. This assists the user in deciding whether or not the drug 26 has been stored for an unsuitable length of time in the drug delivery container 14 and should be discarded.

The reader/indicia-generating device 12 may be positioned proximate where the drug delivery container 14 will be prepared. For example, in an operating room environment, the reader/indicia-generating device 12 may be positioned on the work surface of a drug storage cart, shown at 55 in FIG. 1.

The drug delivery container reader 16 is configured to read the drug-delivery-container-associated machine-readable drug identification indicia 42 and to transfer that information to the processing unit 18. In some embodiments, the drug delivery container reader 16 may be optimized to read the drug-delivery-container-associated machine-readable indicia 42 relatively quickly, permitting the user to administer the drug 26 relatively quickly. For example, in an operating room environment, the drug delivery container 14 may be one or another form of syringe 15, and the indicia 42 may be a bar-code or the like.

To some extent, the indicia 42 on the syringe 15 could be made to not vary significantly in size and orientation from syringe to syringe. Thus, the drug delivery container reader 16 could be optimized to read those indicia 42 relatively quickly and predictably for a given orientation of the syringe 15. Time efficiency in certain environments, such as an operating room environment, can be important, since speed of administering a drug may be important for the well-being, or indeed the survival, of a patient 55.

It has been found that an orbital laser scanner type of bar-code reader operates relatively well as the drug delivery container reader 42 and is capable of reading the bar-code on a syringe over a variety of orientations of the syringe. Thus, the user may be able to easily and quickly scan the syringe 15 so as not to unduly delay the administering of the drug 26 to the patient 55.

The processing unit 18 processes the information and outputs relevant output signals to one or more output devices 20. The output devices 20 may include an audio output device 56, such as a speaker, and/or a visual output device 58, such as a screen. With the visual output device 58, the user passes the drug-delivery-container-associated machine-readable indicia 42 within range of the drug delivery container reader 16 and the processing unit 18 outputs user-comprehensible drug information on the display 58. By reviewing the drug information that is displayed, the user can easily discern whether the drug to be administered is correct. Optionally, other information can also be displayed, such as patient information.

In some embodiments of the system 10, the user may enter some identification of the patient 55 to the processing unit 18 prior to scanning the drugs 26 to be delivered to the patient 55. The identification of the patient 55 may be made any suitable way, such as by typing in the patient's MRN or name using a keyboard 510.

In embodiments with the audio output device 56, the user can pass the drug-delivery-container-associated machine-readable indicia 42 within range of the drug delivery container reader 16, and the audio output device 56 outputs user-comprehensible drug information (eg. drug name) audially. The advantage to using an audio output device 56 is that the user is not required to actively take a moment to look at a screen to receive the information; instead the user can be passive or can be involved in some other action, such as positioning the drug delivery container 14 for drug release, and can still receive the drug information.

In embodiments wherein the system 10 can access the patient's electronic medical record (EMR) from a medical information system 400, the audio and/or visual output devices 56 and 58 may be used to warn the user of a problem with the drug 26 that is scanned at the reader 16. For example, the processing unit 18 can issue a warning by means of one or both of the audio and visual output devices 56 and 58 of one or more of the following conditions: the scanned drug 26 may have a harmful interaction with one or more drugs that the patent 55 is taking; the scanned drug 26 may have a harmful interaction with one or more of the drugs 26 just administered or about to be administered to the patient (if such information is stored by the medical information 400 or the processing unit 18); the scanned drug 26 may cause an allergic reaction in the patient 55; the scanned drug 26 is not among the list of drugs that the patient 55 is expected to receive during the present procedure (if such information is stored by the medical information 400 or the processing unit 18); the scanned drug 26 is not the expected next drug 26 in the list of drugs 26 that the patient 55 is expected to receive during the present procedure (if such information is stored by the medical information 400 or the processing unit 18); and the scanned drug 26 is for a different patient than the patient undergoing the present procedure (if such information is present on the label 28). It will be noted that for some of these conditions to be checked, the processing unit 18 need not access the patient's EMR.

The drug delivery container reader 16 is preferably positioned proximate the drug delivery area. For example, it may be positioned proximate the head of the patient 55 in an operating room environment, as shown in FIG. 1. It will be appreciated that, in an operating room environment, the drug delivery container reader 16 may be positioned in a 'dirty' area of the room and the storage container reader 30 may be positioned in a 'clean' area of the room. Thus, the storage container reader 30 and the drug delivery container reader 16 may be two distinct devices.

Figure 2:
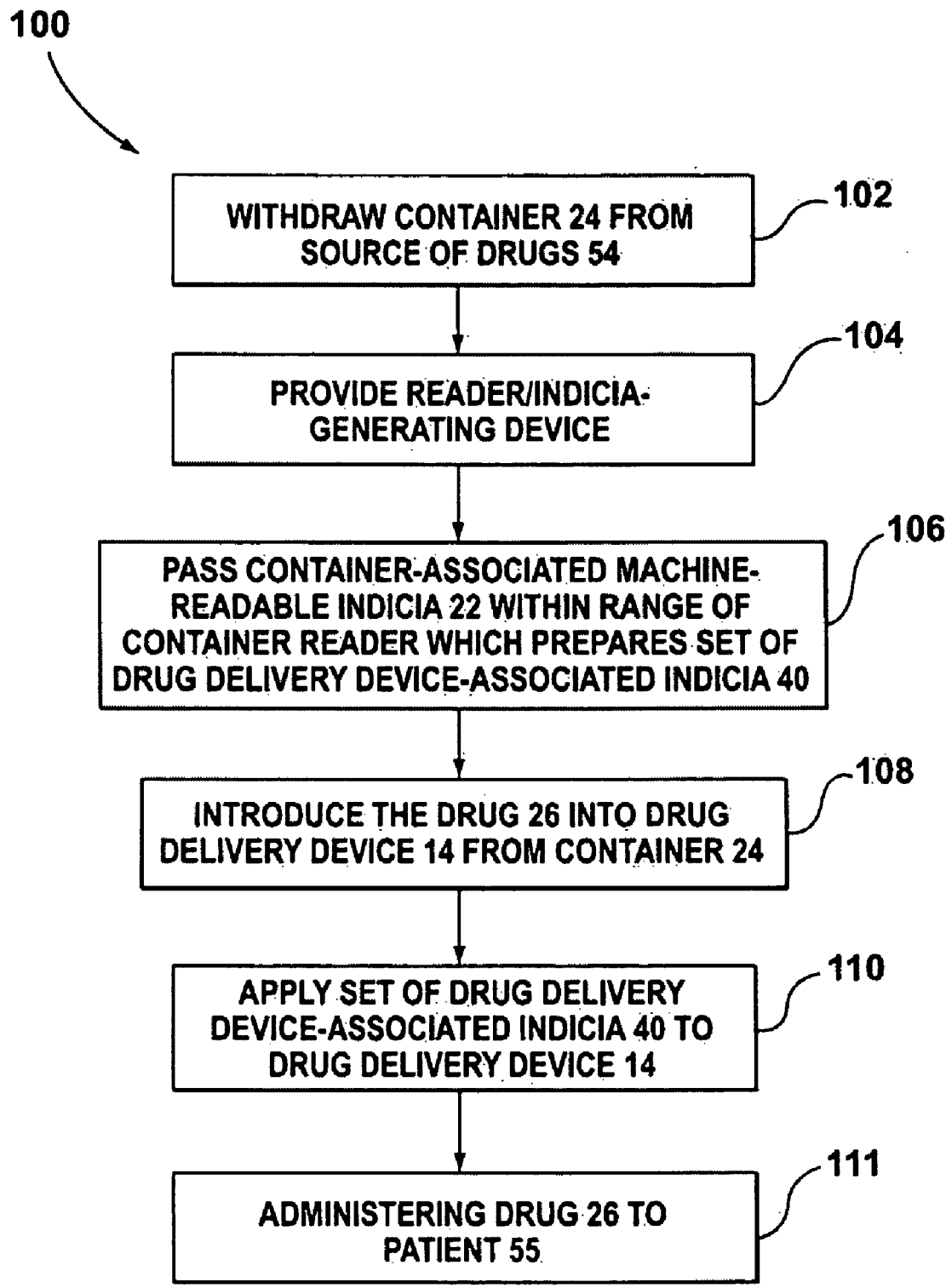
FIG. 2 is a flow-chart illustrating a method for tracking drugs during a transfer and administering process according to another embodiment of the invention.

Reference is made to FIG. 2, which shows a method 100 for tracking drugs during a repackaging and administering process. The method 100 includes step 102, which is withdrawing a storage container 24 (FIG. 1) containing a drug 26 from a source of drugs, such as the drug storage cart 54, wherein the storage container 24 has thereon the storage-container-associated machine-readable indicia 22 identifying the drug 26.

The method 100 (FIG. 2) further includes step 104, which is providing a storage container reader/indicia-generating device including a storage container reader, such as, for example, the storage container reader 30 (FIG. 1), and an indicia-generating device, such as, for example the indicia-generating device 32. The storage container reader is configured to read the storage-container-associated machine-readable indicia 22 identifying a drug 26 and wherein the indicia-generating device 32 is configured to generate a set of one or more drug-delivery-container-associated indicia 40 which identify the drug 26 and which are based on the received container-associated machine-readable indicia 22.

The method 100 (FIG. 2) further includes step 106 which is passing the storage-container-associated machine-readable indicia 22 (FIG. 1) within range of the storage container reader 30 so that the container reader/indicia-generating device reads the indicia 22 and the controller generates an output signal relating to the drug-delivery-container-associated indicia 40. At step 107, (FIG. 2) the drug-delivery-container-associated indicia 40 are generated. At step 108 (FIG. 2) the drug 26 (FIG. 1) is transferred into the drug delivery container 14 from the storage container 24. At step 110 (FIG. 2), the indicia 40 (FIG. 1) are applied to the drug delivery container 14. In some embodiments, such as those where a label 28 is generated by the indicia-generating device, the indicia 40 are applied to the drug delivery container 14 after they are generated by the indicia-generating device 32. In other embodiments, the indicia 40 may be applied directly to the drug delivery container 14 by the indicia-generating device, so that step 108 (FIG. 2) occurs at the same time as the indicia 40 (FIG. 1) are generated.

It will be understood that step 110 (applying indicia 42 to the drug delivery container 14) need not take place after step 108 (transferring drug 26 into the drug delivery container 14). For example, in an embodiment wherein the indicia-generating device 32 is configured to print the indicia 40 directly on the drug delivery container 14, the indicia 40 may be applied as soon as the storage container 24 is passed in range of the storage container reader 30 which may occur while the storage container 24 still contains the drug 26.

However, in an embodiment wherein a label 28 is generated by the indicia-generating device 32, the drug delivery container 14, such as a syringe 15, the user may scan the storage container 24, fill the drug delivery container 14, and then apply the label 28 to the drug delivery container 14, in that order. It is conceivable, however, that the user could scan the storage container 24, apply the label 28 to the drug delivery container 14, and then fill the drug delivery container 14. It is alternatively conceivable, that the user could fill the drug delivery container 14 from the storage container 24, then scan the storage container 24 and then apply the label 28 (or directly apply the indicia 40) to the drug delivery container 14.

At step 111, the drug 26 is administered to the patient 55. The administering of the drug 26 may take place in any number of suitable ways.

Several of the steps of the method 100 may be provided by different people. For example, it is possible that the person who withdraws the storage container 24 from the source of drugs 54 may be different than the person who administers the drug 26 to the patient 55 and may be different than the person who causes the storage-container-associated machine-readable indicia 22 to be read, who causes the indicia-generating device 32 to generate the drug-delivery-container-associated indicia 40 and who transfers the drug 26 to the drug delivery container 14. Accordingly, the method 100 in one embodiment is contemplated to encompass the aforementioned steps of causing the reading of the indicia 22, causing the indicia 40 to be generated and transferring the drug to the drug delivery container 14.

The method 100 (FIG. 2) may take place advantageously at the point of care of the patient 55 (FIG. 1). By practicing the method 100 (FIG. 2) at the point of care, the drug 26 (FIG. 1) is expected to be administered to the patient 55 relatively soon after being transferred into the drug delivery container 14, for example, within an hour, or even within a few minutes of being transferred into the drug delivery container 14. As a result, the drug 26 is less likely to expire during storage in the drug delivery container 14. It is also less likely to become contaminated with micro-bacteria from the environment, or to become contaminated with chemicals from the drug delivery container 14 itself. For example, in some prior art situations where a drug is held in a syringe for a long period of time, chemicals that are present as part of a syringe can leach into the drug contained in the syringe. For example, chemicals present in the material of the body of the syringe, the plunger and/or the plunger seal can leach into the drug in some situations if the drug is stored too long in the syringe. These chemicals can have an adverse effect on the patient 55 in the event that the patient is allergic or otherwise reactive to them. By keeping the storage time of the drug 26 in the syringe 15 relatively short, the risk of introducing unwanted chemicals into the drug 26 is relatively low.

The method 100 (FIG. 2) may include further steps prior to step 111 (the administration of the drug 26 to the patient 55): Step 112 is providing a drug delivery container reader, such as the drug delivery container 16 (FIG. 1), at the point of care of the patient 55. At step 114 (FIG. 2) a processing unit, such as the processing unit 18 (FIG. 1) is provided. At step 116 (FIG. 2) an output device, such as either (or both) of the output devices 56 or 58 shown in FIG. 1 is provided, at the point of care of the patient 55. At step 118 (FIG. 2) the set of one or more drug-delivery-container-associated machine-readable indicia 42 (FIG. 1) is passed within range of the drug delivery container reader 16 to generate the user-comprehensible output signal on the output device 20.

Using the system 10 does not by itself prevent the user from introducing the wrong drug 26 to the drug delivery container 14. However, by using the system 10, and in particular the reader/indicia-generating device 12, the indicia 40 on the drug delivery container 14 corresponds to the drug 26 in the drug delivery container 14 and corresponds to the drug identification indicia 22 on the storage container 24.

Using the system 10, it is nonetheless possible for the user (a doctor) to withdraw the wrong drug storage container 24 from the source of drugs 54, to fill a drug delivery container 14 with it and to administer that drug 26 to the patient. In the event that the patient 55 reacts unexpectedly to the drug 26 given, however, the user can check on the screen 58 what the drug 26 given was, so that appropriate corrective measures can be taken.

This contrasts with some situations of the prior art where the drug delivery container 14 is mislabeled by the user such that it contains a different drug than that which its label indicates. For example, in such a prior art situation, the label may indicate that the correct drug is contained in a syringe, but the syringe in fact contains the wrong drug. When the patient 55 reacts unexpectedly to the drug 26, there is a strong possibility that the doctor would not think that the drug is the cause and then may not take appropriate action to stabilize the patient 55, which could lead to harm or to loss of life of the patient 55.

The system 10, and optionally the reader/indicia-generating device 12 by itself, can be used in other environments than in the operating room. For example, in a critical care environment (eg. a recovery area for patients who have undergone surgery or some other treatment, intensive care unit or an emergency care unit), a drug 26 is administered to a patient 55 by withdrawing a drug storage container 24 from a source of drugs, such as a cabinet or cart 54 that is near the patient 55 (ie. at the point of care), and preparing an appropriate drug delivery container 14, such as a syringe 15, with the drug 26.

Sometimes during such a procedure, the person (eg. a nurse) administering the drug 26 has to put down the syringe 15 during the manual preparation of the syringe label to attend to the patient 55 unexpectedly. When returning to the drug delivery container preparation area, the nurse may come to realize that there is more than one syringe 15 in the preparation area, and is now no longer certain as to which syringe 15 contains which drug 26. By having the reader/indicia-generating device 12 print the drug delivery container indicia 40 automatically, the procedure is hastened so that the nurse is more likely to be able to apply the indicia 40 to the syringe 15 or other drug delivery container 14 without interruption by an unexpected need to attend to the patient 15.

In such an environment, there is no need to have a storage container reader 30 and a drug delivery container reader 16 that are separate from each other. Accordingly, a system 10' shown in FIG. 3, includes a single reader 122 which serves as both the storage container reader and the drug delivery container reader. Additionally, in such an integrated system 10', the optional display 52 may not be needed if there is present the optional visual output device 58. The system 10' may otherwise be similar to the system 10 (FIG. 1).

It has been stated that some of the above described components are advantageously present at the point of care of the patient 55. Being at the point of care of the patient 55 is not limited to meaning immediately adjacent the patient 55. It refers more to being proximate the patient 55. This may in some situations mean being at a nurses station on the same floor of the facility in which the patient is present. It may in some situations mean being in the same room as the patient 55. It may in some situations mean being in the same building as the patient 55. It is, in any case, beneficial for the drug delivery container 14 to be scanned (in embodiments containing a drug delivery container reader 16) proximate the patient 55, just prior to administration of the drug 26 to the patient 55 so as to reduce the likelihood that the drug delivery container 14 will be put down by the nurse, doctor or other user between the drug delivery container scanning 4 step and the drug administering step.

In order to update a patient's EMR, a user of some prior art systems must have the record open for that patient, and must enter the drug name, the drug dosage and the time that the drug was administered if available. In many situations, many drugs must be provided to the patient 55 within a relatively short period of time, however. Due to time constraints, the user may opt to give the patient 55 doses of several drugs 26 and may reconstruct the drug delivery history afterwards when time is more available. In general, however, this can lead to a loss of accuracy of some information with some prior art systems. For example, when reconstructing the drug delivery history after a procedure such as surgery, the user may forget which drugs and what dosages were administered to the patient 55. Additionally, the user may not remember accurately the time at which each of the drugs 26 were delivered.

In general, when trying to reconstruct a drug delivery history, it may be easier for a user to recall dosages given when they are prompted with the names of the drugs given, than it is for the user to remember all the drugs and the associated dosages.

Thus the patient's medical record might be more accurate if at least the drug names could be entered into the EMR and then the user would only have to remember the dosages given later on when reconstructing the drug delivery history. Some prior art systems, however, require the user to entering the drug name manually via keyboard, which can be a time consuming and error prone task, thereby inhibiting the user from doing so at the time of drug delivery. Furthermore, some prior art EMR systems prevent the user from simply entering the names of drugs delivered to the patient without also entering other information such as dosage and time of delivery along with it, which slows down the drug entry process even further when coupled with the already slow process of manually entering the drug name with some prior art systems. Therefore, with some prior art systems, the user is inhibited from entering drug names during the drug delivery process which could have facilitated the reconstruction drug delivery history later.

With the systems 10 and 10', however, the drug names may be entered into a list automatically when the drugs are scanned at the drug delivery container reader 16 or 122. The user may then later review the list and fill in missing information such as the dosages given, which may be easier to remember when prompted with the drug names, as noted above. Furthermore, the list may include time stamps of when the drugs 26 were scanned. This may provide a more accurate representation of when the drugs 26 were administered than relying on the user's memory when reconstructing the drug delivery history afterwards or than simply time stamping the drug delivery as occurring when the drug entry is made, as is done by some prior art systems.

Figure 3:
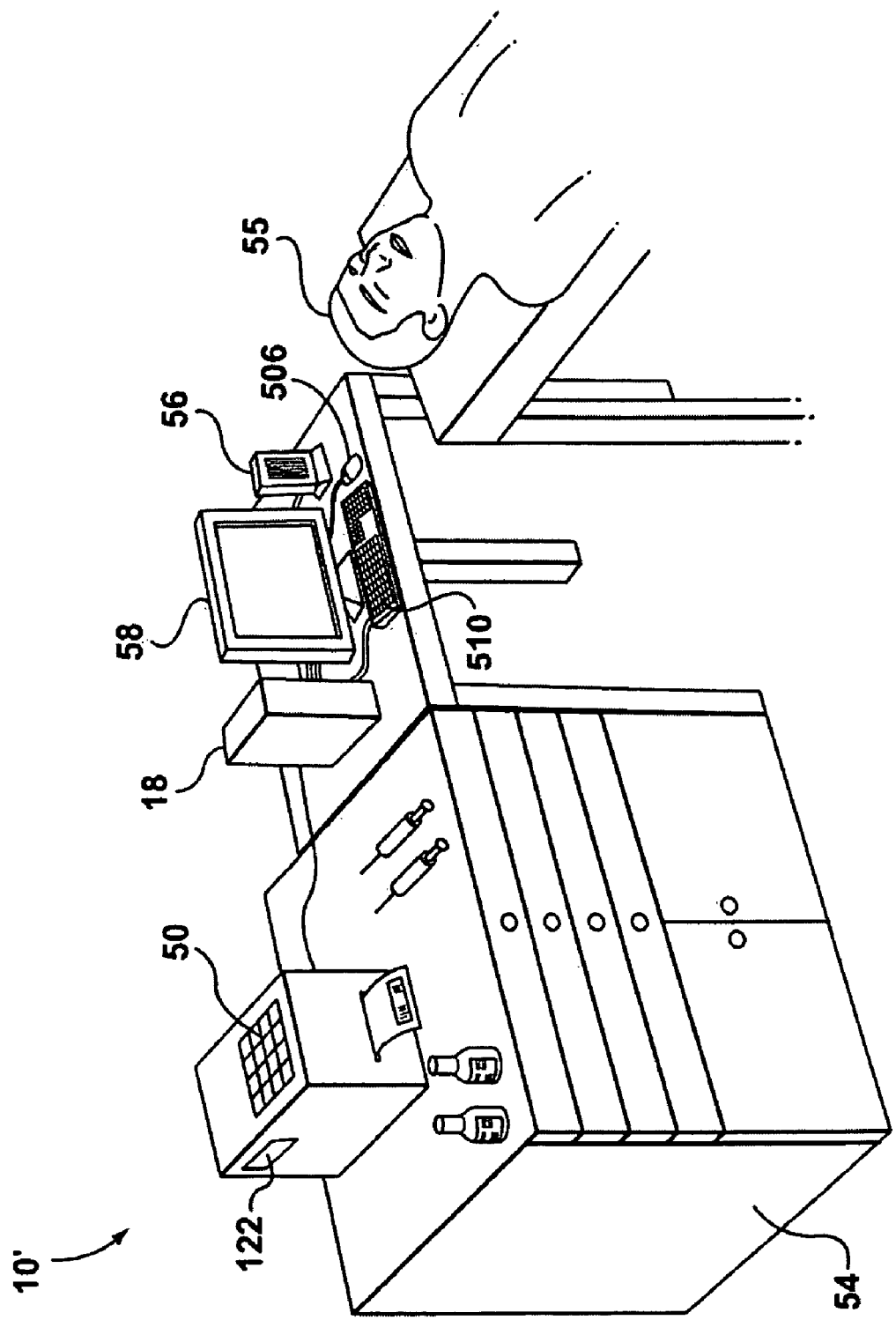
FIG. 3 is a perspective view of a system for tracking drugs during a transfer and administering process in accordance with another embodiment of the invention.
Figure 5:
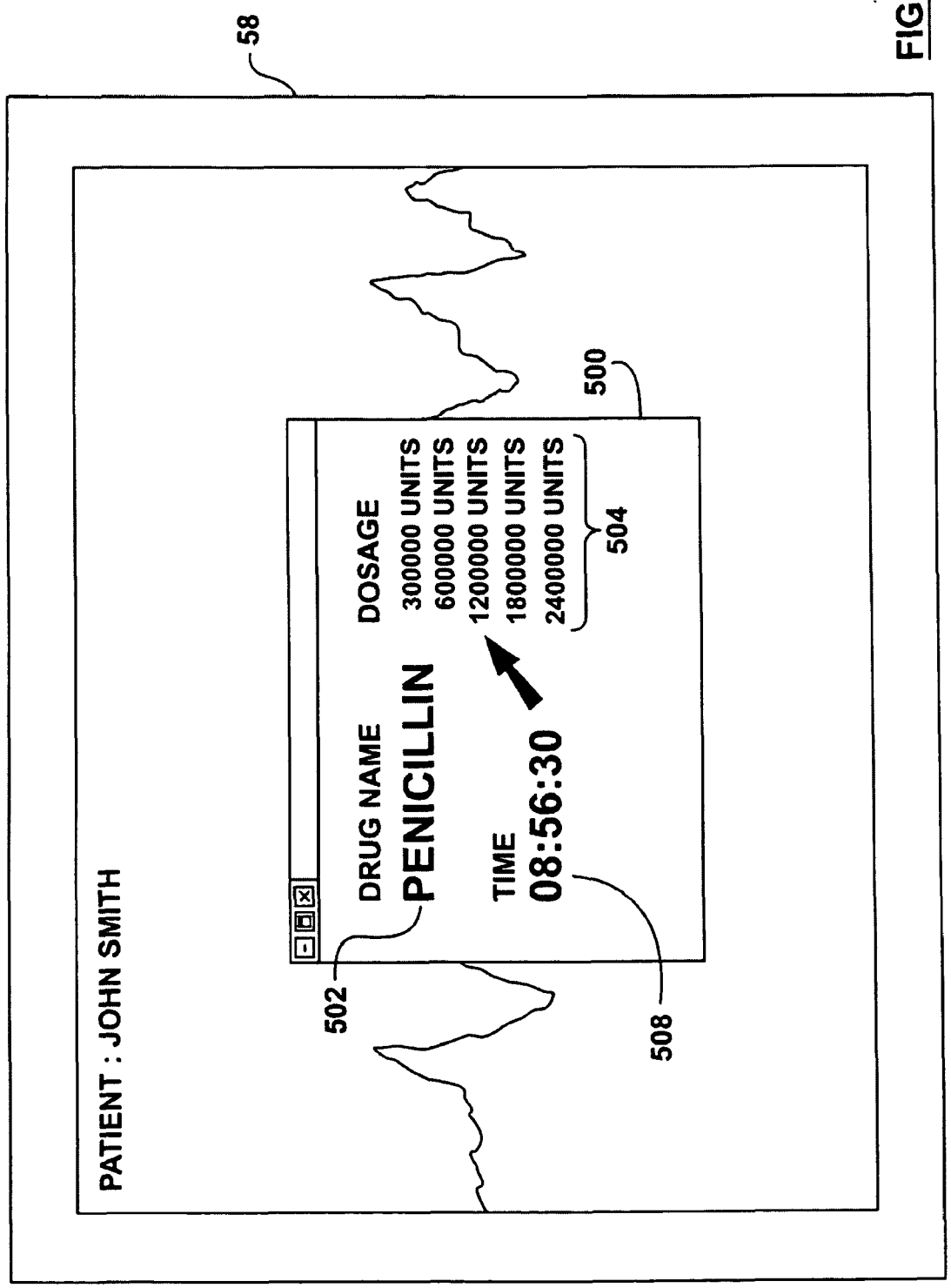
FIG. 5 is an illustration of a visual output device or display used in the system shown in FIG. 1.

It may also be possible for the user to enter the drug delivery information into the system during the drug delivery activity, because the system 10 or 10' simplifies the data entry at least in some embodiments. For example, each time a drug 26 is scanned by the reader 16 or 122, the system 10 or 10' may open a window 500 (see FIG. 5) on the display 58. The window 500 displays the drug name at 502 and may present a short list of likely possible values at 504 for the dosage, to choose from for that drug 26 (FIGS. 1 and 3). Thus, the user may simply choose the correct dosage value 504 (FIG. 5) using a mouse 506 (FIG. 1 or 3), or some other suitable pointer device. The system 10 or 10' may automatically time stamp the drug entry, as shown at 508 in FIG. 5, when the drug 26 (FIG. 1 or 3) was scanned at the reader 16 or 122, or alternatively when the user enters the dosage information in the window 500 (presumably immediately after having given the drug 26). As soon as the dosage information is provided, the system 10 or 10' could update the patient's EMR with the information. Thus, the system 10 or 10' would therefore permit the user to enter a drug into a patent's EMR by simply selecting the dosage of the drug displayed in the window, potentially with a single mouse click. As a result of the ease of use and small amount of data that the user has to enter (ie. only the dosage), the system 10 or 10' permits the user, in some situations, to enter the drugs 26 into the patient's EMR at the time the drugs 26 are given to the patent 55 instead of afterwards. This may reduce the risk that the user forgets the dosages actually given to the patient 55 when attempting to reconstruct the drug delivery history afterwards. Additionally, by time stamping the drug entry when the user enters the dosage information, the time stamp may be even more accurate than time stamping the drug entry at the time that the drug 26 is scanned by the reader 16 or 122, which, as noted above, may itself be more accurate than relying on the user's memory when trying to reconstruct a drug delivery history after surgery using some prior art systems.

In embodiments wherein the system 10 or 10' opens a window on the display 58, the system 10 or 10' may close the window after a selected period of time if the user does not enter the dosage information, so as not to block information that may be displayed behind the window, such as a time graph of the patient's heartbeat, for example.

The drug delivery container 14 has been described as being a syringe 15 by way of example only. The drug delivery container 14 may alternatively be another type of device. For example, the drug delivery container 14 may be a cup for holding a selected quantity of a drug 26 for consumption by the patient 55. Alternatively, the drug delivery container 14 may be, for example, a module which is insertable into a syringe or similar device, wherein the syringe plunger urges the drug 26 out of the module for delivery to the patient 55. As another alternative, the drug delivery container 14 may be a syringe that is configured to feed the drug 26 to an intravenous liquid supply system instead of being configured to inject the drug into the patient 55.

It is possible that a system in accordance with an embodiment of the invention could be provided wherein the indicia-generating device 32 is omitted, such that the system would include the storage container reader 30 and the controller 31, and whereby the system would be connectable to an indicia-generating device provided by the user. In such an embodiment, the system 10 would be used to read a set of one or more storage-container-associated machine-readable drug identification indicia 22 and would generate an output signal to control the output of the indicia-generating device which may be provided by the user. The connection between the system (and more particularly the controller 31) and the indicia-generating device may be a wired connection or a wireless connection.

In general, with any system for tracking drugs 26, it is advantageous for the system to identify a potential problem (eg. drug allergy) at the earliest possible stage. For example, in embodiments of the present invention, it is advantageous for the system 10 or 10' to identify a potential problem (eg. drug allergy) in the first stage where the drugs 26 are scanned by the reader/indicia-generating device 12, rather than identifying a potential problem in the second stage where the drugs are about to be administered and are being scanned by the drug delivery container reader 16. This is because a doctor or other user may be too caught up in the need to take action with a patient and could potentially ignore warnings from the system 10 or 10' and administer a potentially dangerous drug to the patient 55 inadvertently.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein.

We claim:

1. A method for tracking drugs during a transfer and administering process, wherein a drug is transferred from a storage container to a drug delivery container, the storage container having thereon a set of one or more storage-container-associated machine-readable indicia identifying the drug, the method comprising:
   a) accessing storage containers containing different respective drugs at a point of care of a patient to prepare one or more drug delivery containers, the respective drug delivery containers requiring a set of one or more drug delivery container associated indicia, yet to be prepared, corresponding, respectively, to the storage-container-associated machine-readable indicia identifying the respective drugs;
   b) preparing a drug delivery container to contain a drug next designated for transfer to a drug delivery container by:
      (i) providing a reader/indicia-generating device including a storage container reader and an indicia-generating device at the point of care of the patient, wherein the storage container reader is configured to read the set of one or more storage-container-associated machine-readable indicia, and wherein the indicia-generating device is configured to generate a set of one or more drug-delivery-container-associated indicia identifying said drug, based on the set of one or more storage-container-associated machine-readable indicia;
      (ii) causing the storage-container-associated machine-readable indicia to be read by the storage container reader at the point of care of the patient so that the storage container reader/indicia-generating device prepares a set of drug-delivery-container-associated indicia corresponding to said drug at the point of care of the patient;
      (iii) designating a next drug delivery container to which the set of drug-delivery-container-associated indicia corresponding to said drug are to be applied and to which said drug is to be transferred;
      (iv) transferring said drug into the designated next drug delivery container from the storage container at the point of care of the patient; and
      (v) applying the set of one or more drug-delivery-container-associated indicia to the designated next drug delivery container at the point of care of the patient;
   wherein the point of care of the patient is a medical care delivery location configured for immediate administration of drugs to the patient in response to a need of the patient, and wherein, at the time of preparing the designated next drug delivery container to contain said drug transferred from the storage container, only the set of one of more drug-delivery-container-associated indicia identifying said drug, prepared in step b)(ii), is at hand for application to the designated next drug delivery container to which said drug is transferred.

2. A method for tracking drugs as claimed in claim 1, wherein the set of one or more drug-delivery-container-associated indicia includes a set of one or more drug delivery container machine-readable indicia, and wherein the method further comprises:
   c) reading the set of one or more drug delivery container machine-readable indicia at the selected point of care of the patient;
   d) generating an output signal corresponding to the drug based on the set of one or more drug delivery container machine-readable indicia that has been read; and
   e) outputting a user-comprehensible output identifying the drug based on the output signal.

3. A method for tracking drugs as claimed in claim 1, wherein the set of one or more storage-container-associated machine-readable indicia is a bar-code.

4. A method for tracking drugs as claimed in claim 1, wherein the drug delivery container is a syringe.

5. A method for tracking drugs as claimed in claim 1, wherein the storage container is a unit-dose container.

6. A method for tracking drugs as claimed in claim 1, wherein step b) includes preparing a self-adhesive label with the drug delivery container indicia thereon, and step e) includes applying the label to the drug delivery container.

7. A method for tracking drugs as claimed in claim 1, further comprising administering the drug to the patient within an hour of performing step b).

8. A method according to claim 1, wherein steps a) and b) are carried out after a determination is made that the drug is needed for treating a patient.

9. A method according to claim 1, wherein steps a) and b) are carried out in an operating room during the course of surgery.

10. A point of care system for tracking drugs during a transfer and administering process, comprising:
    a source of drugs including a set of storage containers each containing one drug of a plurality of drugs, wherein a need to administer any one drug of the plurality of drugs may arise at a point of care of a patient in response to a need of the patient;
    a storage container reader configured to read a set of one or more storage-container-associated machine-readable indicia on the storage containers, wherein the set of one or more storage-container-associated machine-readable indicia on each of the storage containers identifies the one drug that is in that storage container;
    an indicia-generating device configured to generate a set of one or more drug-delivery-container-associated indicia identifying a drug based on the storage-container-associated machine-readable indicia, wherein the set of one or more drug-delivery-container-associated indicia includes machine-readable indicia; and
    a drug delivery container reader configured to read the set of one or more drug-delivery-container-associated machine-readable indicia;
    wherein the point of care is a location configured for immediate administration of drugs in response to a need of the patient, and wherein the source of drugs, the storage container reader, the indicia generating device, and the drug delivery container reader are configured to be positioned in said location, such that at a time of preparation of a drug delivery container to receive a drug transferred from one of the storage containers, the set of one or more drug-delivery-container-associated indicia corresponding to said drug can be generated in said location so as to be the only set of drug-delivery-container-associated indicia then at hand for application to the drug delivery container to which said drug is transferred.

11. A point-of-care system according to claim 10, further comprising:
    a processing unit configured to generate an output signal corresponding to the drug based on the set of one or more drug-delivery-container-associated machine-readable indicia; and an output device configured to output a user-comprehensible output identifying the drug based on the output signal from the processing unit;

wherein the processing unit and the output device are configured to be positioned in said location.

12. A point of care system for tracking drugs as claimed in claim 11, wherein the output device includes a visual output device for displaying a name of the drug.

13. A point of care system for tracking drugs as claimed in claim 11, wherein the output device includes a speaker operable for audibly outputting a name of the drug.

14. A point-of-care system according to claim 10, further comprising a user input interface configured for entering additional information in association with the storage container machine readable indicia during the transfer and administration process, the indicia-generating device being configured to generate a set of one or more drug-delivery-container-associated indicia reproducing the additional information.

15. A point-of-care system according to claim 14, wherein the drug delivery container is a syringe, and wherein the additional information comprises one or more of the volume of a diluent added to a drug, a type of diluent added to a drug, and an exact volume of a drug drawn into the syringe.

16. A point of care system for tracking drugs as claimed in claim 10, wherein the drug delivery container reader and the storage container reader are the same reader.

17. A point of care system for tracking drugs as claimed in claim 10, wherein the drug delivery container reader and the storage container reader are separate from each other.

18. A method for tracking drugs during a transfer and administering process, wherein a drug is transferred from a storage container to a drug delivery container, the storage container having thereon a set of one or more storage-container-associated machine-readable indicia identifying the drug, the method comprising:

a) accessing storage containers containing different respective drugs at a point of care of a patient to prepare one or more drug delivery containers, the respective drug delivery containers requiring a set of one or more drug delivery container associated indicia, yet to be prepared, corresponding, respectively, to the storage-container-associated machine-readable indicia, identifying the respective drugs; and b) preparing a drug delivery container to contain a drug next designated for transfer to a drug delivery container by:

(i) providing a reader/indicia-generating device including a storage container reader and an indicia-generating device at the point of care of the patient, wherein the storage container reader is configured to read the set of one or more storage-container-associated machine-readable indicia, and wherein the indicia-generating device is configured to generate a set of one or more drug-delivery-container-associated indicia identifying said drug, based on the set of one or more storage-container-associated machine-readable indicia;

(ii) causing the storage-container-associated machine-readable indicia to be read by the storage container reader at the point of care of the patient so that the storage container reader/indicia-generating device prepares a set of drug-delivery-container-associated indicia corresponding to said drug at the point of care of the patient;

(iii) designating a next drug delivery container to which the set of drug-delivery-container-associated indicia corresponding to said drug are to be applied and to which said drug is to be transferred;

(iv) transferring said drug into the designated next drug delivery container from the storage container at the point of care of the patient; and (v) applying the set of one or more drug-delivery-container-associated indicia to the designated next drug delivery container at the point of care of the patient;

wherein the point of care of the patient is a medical care delivery location configured for immediate administration of drugs to the patient in response to a need of the patient, and wherein the set of one of more drug-delivery-container-associated indicia prepared in step b)(ii), is applied to said designated next drug delivery container to which said drug is transferred, as per step b)(v), prior to preparing one or more drug-delivery-container-associated indicia for application to any subsequently designated drug and drug delivery container.

19. A method for tracking drugs as claimed in claim 18, wherein the set of one or more drug-delivery-container-associated indicia includes a set of one or more drug delivery container machine-readable indicia, and wherein the method further comprises:

c) reading the set of one or more drug delivery container machine-readable indicia at the point of care of the patient;

d) generating an output signal corresponding to the drug based on the set of one or more drug delivery container machine-readable indicia that has been read; and e) outputting a user-comprehensible output identifying the drug based on the output signal.

20. A method for tracking drugs as claimed in claim 18, wherein the set of one or more storage-container-associated machine-readable indicia is a bar-code.

21. A method for tracking drugs as claimed in claim 18, wherein the drug delivery container is a syringe.

22. A method for tracking drugs as claimed in claim 18, wherein the storage container is a unit-dose container.

23. A method for tracking drugs as claimed in claim 18, wherein step b) includes preparing a self-adhesive label with the drug delivery container indicia thereon, and applying the label to the drug delivery container.

24. A method for tracking drugs as claimed in claim 18, further comprising administering the drug to the patient within an hour of performing step b).

25. A method according to claim 18, wherein steps a) and b) are carried out on after a determination is made that the drug is needed for treating a patient.

26. A method according to claim 18, wherein steps a) and b) are carried out in an operating room during the course of surgery.

* * * * *